US011070787B2

(12) United States Patent
Medal et al.

(10) Patent No.: US 11,070,787 B2
(45) Date of Patent: *Jul. 20, 2021

(54) AUGMENTED OPTICAL IMAGING SYSTEM FOR USE IN MEDICAL PROCEDURES

(71) Applicant: Synaptive Medical Inc., Toronto (CA)

(72) Inventors: Thomas Alexander Medal, Toronto (CA); Gal Sela, Toronto (CA)

(73) Assignee: Synaptive Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/038,158

(22) Filed: Sep. 30, 2020

(65) Prior Publication Data
US 2021/0037228 A1 Feb. 4, 2021

Related U.S. Application Data

(63) Continuation of application No. 16/384,075, filed on Apr. 15, 2019, now Pat. No. 10,827,162.

(51) Int. Cl.
*A61B 34/30* (2016.01)
*H04N 13/204* (2018.01)
*G02B 21/00* (2006.01)
*G02B 21/22* (2006.01)
*G02B 21/36* (2006.01)
*H04N 13/111* (2018.01)
*A61B 90/20* (2016.01)
*A61B 90/50* (2016.01)
*H04N 13/156* (2018.01)
(Continued)

(52) U.S. Cl.
CPC ........... *H04N 13/204* (2018.05); *A61B 34/30* (2016.02); *A61B 90/20* (2016.02); *A61B 90/50* (2016.02); *G02B 21/0012* (2013.01); *G02B 21/22* (2013.01); *G02B 21/361* (2013.01); *G02B 21/367* (2013.01); *H04N 13/111* (2018.05); *H04N 13/156* (2018.05); *A61B 2090/103* (2016.02); *A61B 2090/3618* (2016.02); *A61B 2090/371* (2016.02); *A61B 2090/373* (2016.02)

(58) Field of Classification Search
None
See application file for complete search history.

(56) References Cited

U.S. PATENT DOCUMENTS 6,020,993 A 2/2000 Greenberg
6,369,831 B1 4/2002 Baba et al.
(Continued)

OTHER PUBLICATIONS

WIPO: International Search Report & Written Opinion relating to PCT application No. PCT/CA2020/050500, dated Jul. 9, 2020.

*Primary Examiner* — Eileen M Adams
(74) *Attorney, Agent, or Firm* — Rowand LLP

(57) ABSTRACT

An optical imaging system for imaging a target during a medical procedure is disclosed. The optical imaging system includes: a first camera for capturing a first image of the target; a second wide-field camera for capturing a second image of the target; at least one path folding mirror disposed in an optical path between the target and a lens of the second camera; and a processing unit for receiving the first image and the second image, the processor being configured to: apply an image transform to one of the first image and the second wide-field image; and combine the transformed image with the other one of the images to produce a stereoscopic image of the target.

20 Claims, 12 Drawing Sheets

(51) Int. Cl.
  *A61B 90/10*     (2016.01)
  *A61B 90/00*     (2016.01)

(56) References Cited

U.S. PATENT DOCUMENTS

| | | | |
|---|---|---|---|
| 10,827,162 B1* | 11/2020 | Medal | A61B 90/50 |
| 2010/0103247 A1 | 4/2010 | Lim et al. | |
| 2011/0001973 A1* | 1/2011 | Polidor | G03B 21/28 |
| | | | 356/393 |
| 2017/0339400 A1* | 11/2017 | Hall | H04N 5/247 |
| 2018/0075593 A1* | 3/2018 | Wang | G06T 7/85 |
| 2018/0289428 A1 | 10/2018 | Lee et al. | |
| 2019/0206072 A1* | 7/2019 | Geissler | G01S 5/163 |
| 2019/0290297 A1* | 9/2019 | Haider | A61B 34/20 |

\* cited by examiner

AUGMENTED OPTICAL IMAGING SYSTEM FOR USE IN MEDICAL PROCEDURES

TECHNICAL FIELD

The present disclosure relates to medical imaging and, in particular, to optical imaging systems suitable for use in image-guided medical procedures.

BACKGROUND

Digital microscopes support advanced visualization during medical procedures. For example, digital surgical microscopes provide magnified views of anatomical structures during a surgery. Digital microscopes use optics and digital (e.g. CCD-based) cameras to capture images in real-time and output the images to displays for viewing by a surgeon, operator, etc.

In image-guided medical applications, such as surgery or diagnostic imaging, accurate three-dimensional (3-D) visualization of patient anatomy and surgical tools is crucial. It would be desirable to provide lightweight digital microscope solutions that support accurate 3-D visualization.

BRIEF DESCRIPTION OF DRAWINGS

Reference will now be made, by way of example, to the accompanying drawings which show example embodiments of the present application and in which.

Like reference numerals are used in the drawings to denote like elements and features.

DETAILED DESCRIPTION OF EXAMPLE EMBODIMENTS

Figure 1:
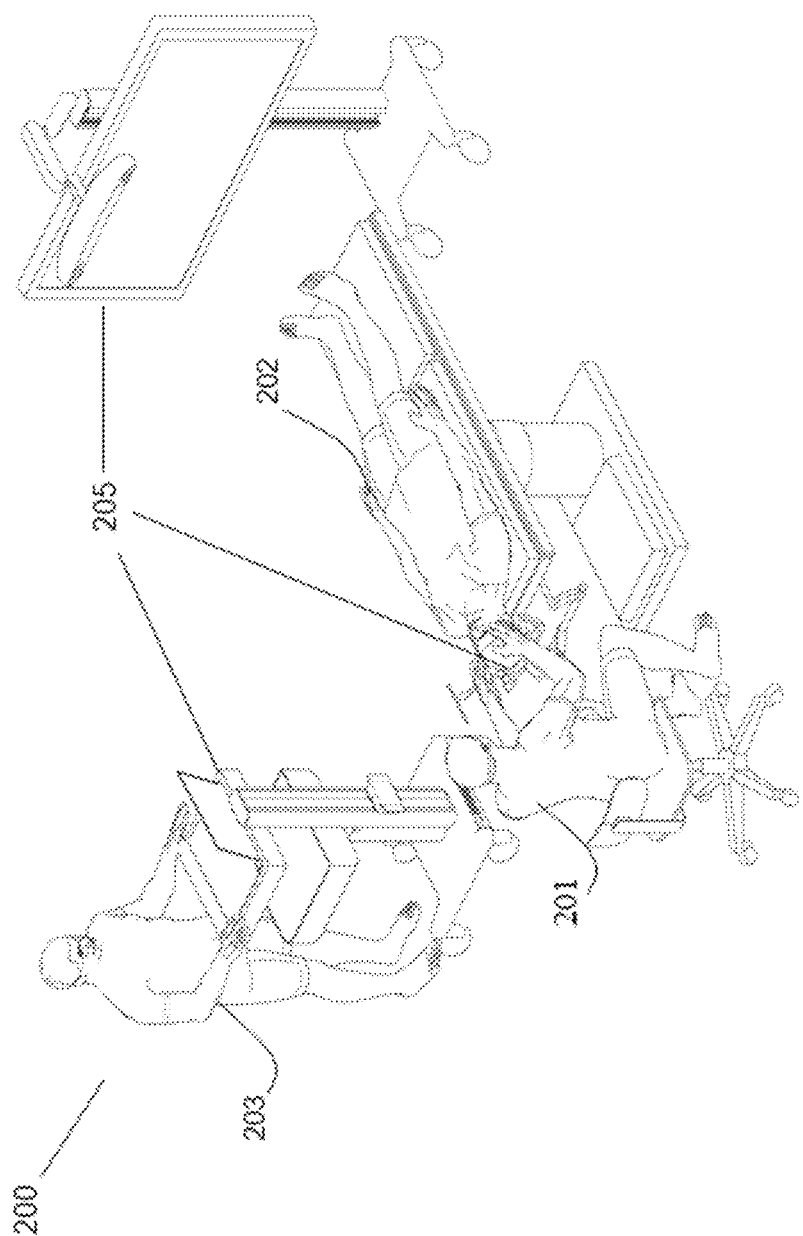
FIG. 1 shows an example navigation system to support image-guided surgery.

In one aspect, the present disclosure describes an optical imaging system for imaging a target during a medical procedure. The optical imaging system includes: a first camera for capturing a first image of the target; a second wide-field camera for capturing a second image of the target; at least one path folding mirror disposed in an optical path between the target and a lens of the second camera; and a processing unit for receiving the first image and the second image, the processing unit being configured to: apply an image transform to one of the first image and the second image; and combine the transformed image with the other one of the images to produce a stereoscopic image of the target.

In some implementations, the first camera, the second camera, and the at least one path folding mirror may be housed within a single housing.

In some implementations, the second camera and the at least one path folding mirror may be included in an add-on module for mounting to the first camera.

In some implementations, the at least one path folding mirror may comprise a first mirror and a second mirror that are selectively positioned based on a position of the lens of the second camera, the first mirror and the second mirror being angled with respect to each other.

In some implementations, the first mirror may be selectively positioned and angled with respect to the target so as to reflect an image of the target to the second mirror, and the second mirror may be selectively positioned and angled so as to reflect the image of the target from the first mirror to the lens of the second camera.

In some implementations, the first camera and the second camera may be positioned such that an optical axis of the first camera is co-planar with the optical axis of the second camera.

In some implementations, the image transform may be a homographic transform.

In some implementations, the processing unit may be further configured to: determine a working distance between the target and an aperture of the optical imaging system; and determine the image transform based on the working distance.

In some implementations, the optical imaging system may be configured to be mountable onto a moveable support structure.

In some implementations, the optical imaging system may further comprise a support connector to enable the optical imaging system to be removably mounted onto the moveable support structure.

In some implementations, the moveable support structure may comprise one of a robotic arm, a manually-operated support arm, or a moveable support frame.

In some implementations, the optical imaging system may further include a manual release button that, when actuated, enables the optical imaging system to be positioned manually.

In some implementations, the processing unit may be responsive to control input received via a user interface.

In some implementations, the optical imaging system may further include one or more light sources.

In some implementations, the second camera may have at least one of fixed zoom optics or fixed focus optics.

In some implementations, the second camera may be fixedly coupled to the first camera.

In another aspect, the present disclosure describes a method of generating a stereoscopic image of a target in a medical procedure using an optical imaging system. The method includes: receiving, from a first camera of the optical imaging system, a first image of the target; receiving, from a second camera of the optical imaging system, a second image of the target; applying an image transform to one of the first image and the second image; and combining the transformed image with the other one of the images to produce the stereoscopic image of the target.

In some implementations, the method may further include determining a working distance between the target and an aperture of the optical imaging system; and determining the image transform based on the working distance.

In some implementations, the method may further include selecting the first homographic transform from a plurality of homographic transforms, wherein the selecting comprises: for each of the plurality of homographic transforms: applying the homographic transform to the second image; computing an image correspondence metric between the transformed second image and the first camera, and selecting the homographic transform having a highest value of image correspondence metric from the plurality of homographic transforms as the first homographic transform.

Other example embodiments of the present disclosure will be apparent to those of ordinary skill in the art from a review of the following detailed descriptions in conjunction with the drawings.

In the present application, the phrase "access port" is intended to refer to a cannula, a conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

In the present application, the term "intraoperative" is intended to refer to an action, process, method, event, or step that occurs or is carried out during at least a portion of a medical procedure. Intraoperative, as defined herein, is not limited to surgical procedures, and may refer to other types of medical procedures, such as diagnostic and therapeutic procedures.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Various medical procedures, such as surgery and diagnostic imaging, employ digital microscopes, which provide magnified views of anatomical structures in real-time. Typically, digital microscope systems incorporate a single main camera (or video-scope) for capturing images which are output to a display for viewing by a surgeon or operator. The main camera provides a single feed of video data, and the frames of the video feed are presented as two-dimensional images. As a result, 3-D visualization and, more specifically, depth perception may be absent in these limited digital microscope systems.

In order to generate 3-D visualization, a second camera may be added to a digital microscope. The images from the two cameras can be combined to produce stereoscopic views of a surgical site. One of the challenges in providing a 3-D capable digital microscope is integrating two cameras such that the microscope maintains a minimal profile in the operative field. A simplistic arrangement of the two cameras side-by-side may render the microscope bulky and may result in significant obstruction of the surgeon's view. A small footprint for the camera modules of the digital microscope offers a large working area for the surgeon.

Furthermore, the size of the cameras and optics may prevent the two cameras of the digital microscope from being arranged close to each other. In particular, there may be physical restrictions to controlling the spacing between the optical paths of the two cameras. This can result in undesirable disparity of images from the cameras and, as a consequence, less successful or comfortable 3-D visualization experience.

The present disclosure provides an augmented optical imaging system for use in medical applications. The disclosed optical imaging system may, for example, be implemented as part of a digital microscope. The system employs a pair of cameras, including a primary camera and an outrigger camera, for imaging a target during a medical procedure. The system also includes at least one path folding mirror which is selectively positioned between the target and a lens of the outrigger camera. The path folding mirrors allow the optical path of the outrigger camera to be manipulated such that the separate optical paths of the two cameras are substantially parallel to each other near the target. The system provides a 3-D visualization of the target by combining video/image frames from the two cameras to produce stereoscopic images of the target.

The present disclosure also provides an optics module for extending the functionalities of a digital microscope system. The disclosed optics module may be an add-on component to an existing optical imaging device, such as a digital microscope. The module includes an outrigger camera and at least one path folding mirror. The path folding mirrors are disposed in an optical path between a lens of the outrigger camera and a target being imaged. The module is configured to be connected to the optical imaging device. For example, the module may define a chamber for receiving a primary camera (e.g. video-scope) of the optical imaging device such that both the primary camera and the outrigger camera are directed towards the target when the module is secured to the optical imaging device. With a minimal profile in the working field, the disclosed optics module allows the combined optical imaging system to produce 3-D visualization of a target.

Reference is first made to FIG. 1, which shows an example navigation system 200. The example navigation system 200 may be used to support image-guided surgery. As shown in FIG. 1, a surgeon 201 conducts a surgery on a patient 202 in an operating room environment. A medical navigation system 205 may include an equipment tower, tracking system, displays, and tracked instruments to assist the surgeon 201 during a procedure. An operator 203 may also be present to operate, control, and provide assistance for the medical navigation system 205.

Figure 2:
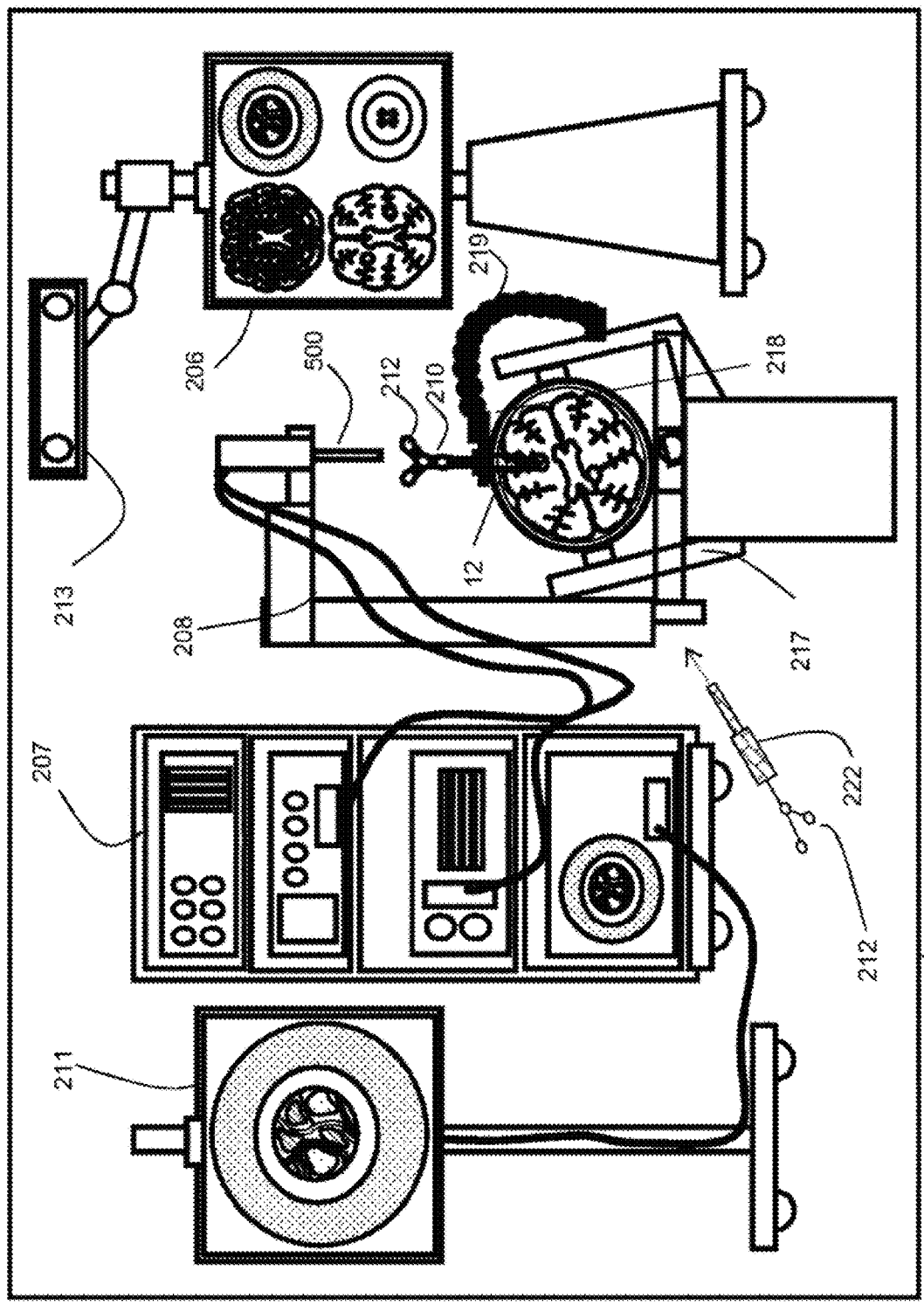
FIG. 2 illustrates components of an example navigation system.

FIG. 2 shows components of an example medical navigation system 205. The disclosed augmented optical imaging system may be used in the context of the medical navigation system 205. The medical navigation system 205 may include one or more displays 206, 211 for displaying video images, an equipment tower 207, and a positioning system 208, such as a medical arm, which may support an optical imaging system 500. One or more of the displays 206, 211 may include a touch-sensitive display for receiving touch input. The equipment tower 207 may be mounted on a frame, such as a rack or cart, and may contain a power supply and a computer/controller that may execute planning software, navigation software, and/or other software to manage the positioning system 208. In some examples, the equipment tower 207 may be a single tower configuration operating with dual displays 206, 211; however, other configurations (e.g. dual tower, single display etc.) may also exist.

A portion of the patient's anatomy may be held in place by a holder. For example, as shown in FIG. 2, the patient's head and brain may be held in place by a head holder 217. An access port 12 and associated introducer 210 may be inserted into the head, to provide access to a surgical site in the head. The optical imaging system 500 may be used to view down the access port 12 at a sufficient magnification to allow for enhanced visibility down the access port 12. The output of the optical imaging system 500 may be received by one or more computers or controllers to generate a view that may be depicted on a visual display (e.g. one or more displays 206, 211).

In some examples, the navigation system 205 may include a tracked pointer 222. The tracked pointer 222, which may include markers 212 to enable tracking by a tracking camera 213, may be used to identify points (e.g. fiducial points) on a patient. An operator, typically a nurse or the surgeon 201, may use the tracked pointer 222 to identify the location of points on the patient 202, in order to register the location of selected points on the patient 202 in the navigation system 205. In some embodiments, a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Fiducial markers 212 may be connected to the introducer 210 for tracking by the tracking camera 213, which may provide positional information of the introducer 210 from the navigation system 205. In some examples, the fiducial markers 212 may be alternatively or additionally attached to the access port 12. In some examples, the tracking camera 213 may be a 3-D infrared optical tracking stereo camera. In some other examples, the tracking camera 213 may be an electromagnetic system (not shown), such as a field transmitter that may use one or more receiver coils located on the tool(s) to be tracked. A known profile of the electromagnetic field and known position of receiver coil(s) relative to each other may be used to infer the location of the tracked tool(s) using the induced signals and their phases in each of the receiver coils.

Location data of the positioning system 208 and/or access port 12 may be determined by the tracking camera 213 by detection of the fiducial markers 212 placed on or otherwise in fixed relation (e.g. in rigid connection) to any of the positioning system 208, the access port 12, the introducer 210, the tracked pointer 222 and/or other tracked instruments. The fiducial marker(s) 212 may be active or passive markers. A display 206, 2011 may provide an output of the computed data of the navigation system 205. In some examples, the output provided by the display 206, 211 may include axial, sagittal, and coronal views of patient anatomy as part of a multi-view output.

The active or passive fiducial markers 212 may be placed on tools (e.g. the access port 12 and/or the optical imaging system 500) to be tracked, to determine the location and orientation of these tools using the tracking camera 213 and navigation system 205. The markers 212 may be captured by a stereo camera of the tracking system to give identifiable points for tracking the tools. A tracked tool may be defined by a grouping of markers 212, which may define a rigid body to the tracking system. This may in turn be used to determine the position and/or orientation in 3-D of a tracked tool in a virtual space. The position and orientation of the tracked tool in 3-D may be tracked in six degrees of freedom (e.g. x, y, z coordinates and pitch, yaw, roll rotations), in five degrees of freedom (e.g. x, y, z, coordinate and two degrees of free rotation), but preferably tracked in at least three degrees of freedom (e.g. tracking the position of the tip of a tool in at least x, y, z coordinates). In typical use with navigation systems, at least three markers 212 are provided on a tracked tool to define the tool in virtual space; however, it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. In some examples, the spatial position and orientation of the tracked tool and/or the actual and desired position and orientation of the positioning system 208 may be determined by optical detection using a camera. The optical detection may be done using an optical camera, rendering the markers 212 optically visible.

In some examples, the markers 212 (e.g. reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 205. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 205. The markers 212 may be tracked relative to a reference point or reference object in the operating room, such as the patient 202.

In some examples, the markers 212 may include printed or 3-D designs that may be used for detection by an auxiliary camera, such as a wide-field camera (not shown) and/or the optical imaging system 500. Printed markers may also be used as a calibration pattern, for example to provide distance information (e.g. 3-D distance information) to an optical detector. Printed identification markers may include designs such as concentric circles with different ring spacing and/or different types of bar codes, among other designs. In some examples, in addition to or in place of using markers 212, the contours of known objects (e.g. the side of the access port 12) could be captured by and identified using optical imaging devices and the tracking system.

A guide clamp 218 (or more generally a guide) for holding the access port 12 may be provided. The guide clamp 218 may allow the access port 12 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g. on another patient support, such as on the surgical bed), to ensure that when locked in place, the guide clamp 218 does not move relative to the patient's head.

In a surgical operating room/theatre, setup of a navigation system may be relatively complicated; there may be many pieces of equipment associated with the surgical procedure, as well as elements of the navigation system 205. Further, setup time typically increases as more equipment is added. To assist in addressing this, the navigation system 205 may include two additional wide-field cameras to enable video overlay information. Video overlay information can then be inserted into displayed images, such as images displayed on one or more of the displays 206, 211. The overlay information may illustrate the physical space where accuracy of the 3-D tracking system (which is typically part of the navigation system) is greater, may illustrate the available range of motion of the positioning system 208 and/or the optical imaging system 500, and/or may help to guide head and/or patient positioning.

The navigation system 205 may provide tools to the neurosurgeon that may help to provide more relevant information to the surgeon, and may assist in improving performance and accuracy of port-based neurosurgical operations. Although described in the present disclosure in the context of port-based neurosurgery (e.g. for removal of brain tumors and/or for treatment of intracranial hemorrhages (ICH)), the navigation system 205 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, among others. The same navigation system 205 may be used for carrying out any or all of these procedures, with or without modification as appropriate.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 205.

Figure 3:
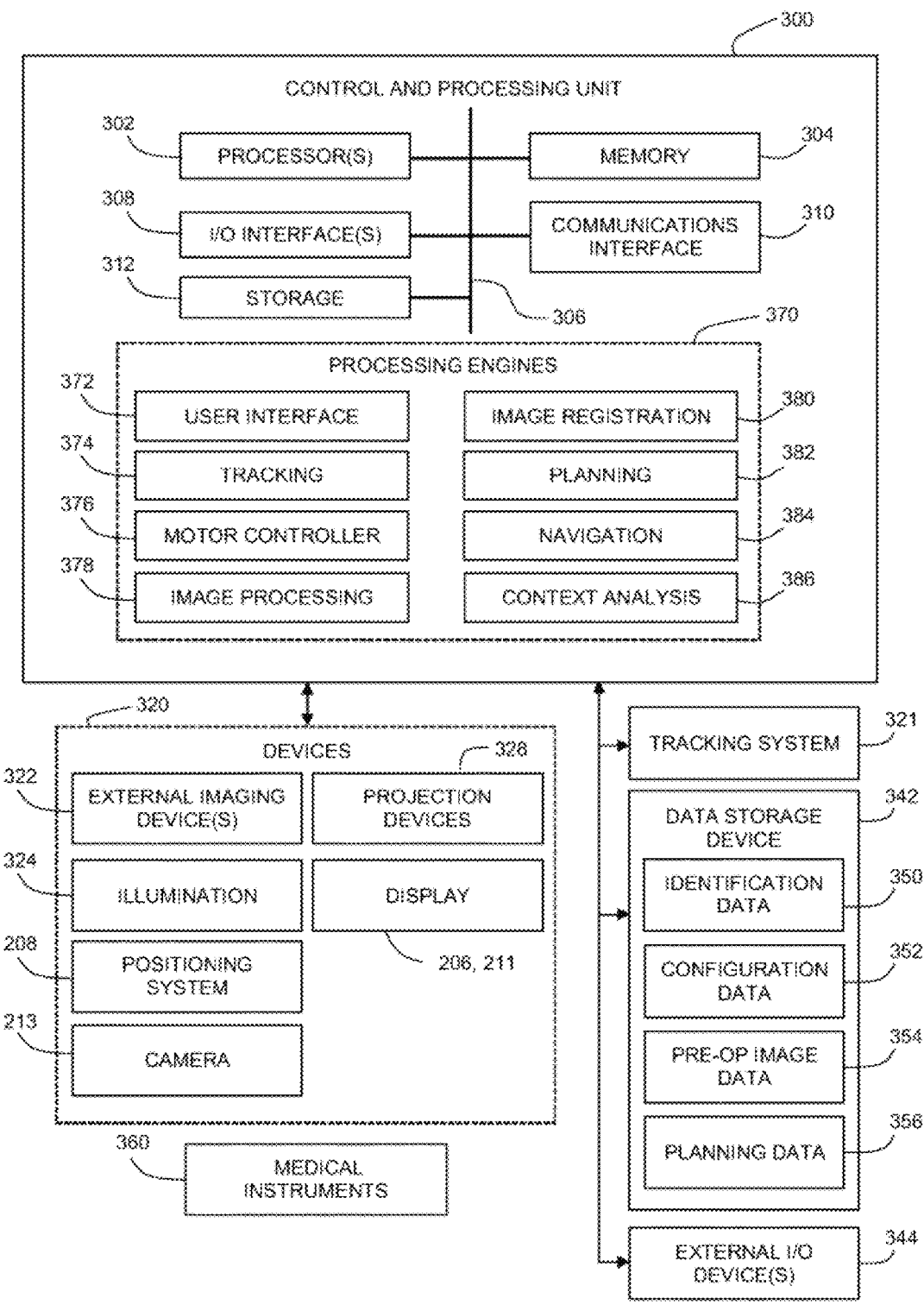
FIG. 3 is a block diagram illustrating an example control and processing system which may be used in the example navigation system of FIGS. 1 and 2.

FIG. 3 is a block diagram illustrating a control and processing system 300 that may be used in the medical navigation system 205 shown in FIG. 2 (e.g. as part of the equipment tower 207). As shown in FIG. 3, the control and processing system 300 may include one or more processors 302, a memory 304, a system bus 306, one or more input/output interfaces 308, a communications interface 310, and storage device 312. The control and processing system 300 may interface with other external devices, such as a tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. The data storage device 342 may also include preoperative image data 354 and/or medical procedure planning data 356. Although the data storage device 342 is shown as a single device in FIG. 3, it will be understood that in other embodiments, the data storage device 342 may be provided as multiple storage devices.

The medical instruments 360 may be identifiable by the control and processing unit 300. The medical instruments 360 may be connected to and controlled by the control and processing unit 300, or the medical instruments 360 may be operated or otherwise employed independent of the control and processing unit 300. The tracking system 321 may be employed to track one or more medical instruments 360 and spatially register the one or more tracked medical instruments to an intraoperative reference frame. For example, the medical instruments 360 may include tracking markers such as tracking spheres that may be recognizable by the tracking camera 213. In one example, the tracking camera 213 may be an infrared (IR) tracking camera. In another example, a sheath placed over a medical instrument 360 may be connected to and controlled by the control and processing unit 300.

The control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, the positioning system 208, the tracking camera 213, one or more projection devices 328, and one or more displays 206, 211.

Exemplary aspects of the disclosure can be implemented via the processor(s) 302 and/or memory 304. For example, the functionalities described herein can be partially implemented via hardware logic in the processor 302 and partially using the instructions stored in the memory 304, as one or more processing modules or engines 370. Example processing modules include, but are not limited to, a user interface engine 372, a tracking module 374, a motor controller 376, an image processing engine 378, an image registration engine 380, a procedure planning engine 382, a navigation engine 384, and a context analysis module 386. While the example processing modules are shown separately in FIG. 3, in some examples the processing modules 370 may be stored in the memory 304 and the processing modules 370 may be collectively referred to as processing modules 370. In some examples, two or more modules 370 may be used together to perform a function. Although depicted as separate modules 370, the modules 370 may be embodied as a unified set of computer-readable instructions (e.g. stored in the memory 304) rather than distinct sets of instructions.

Figure 4A:
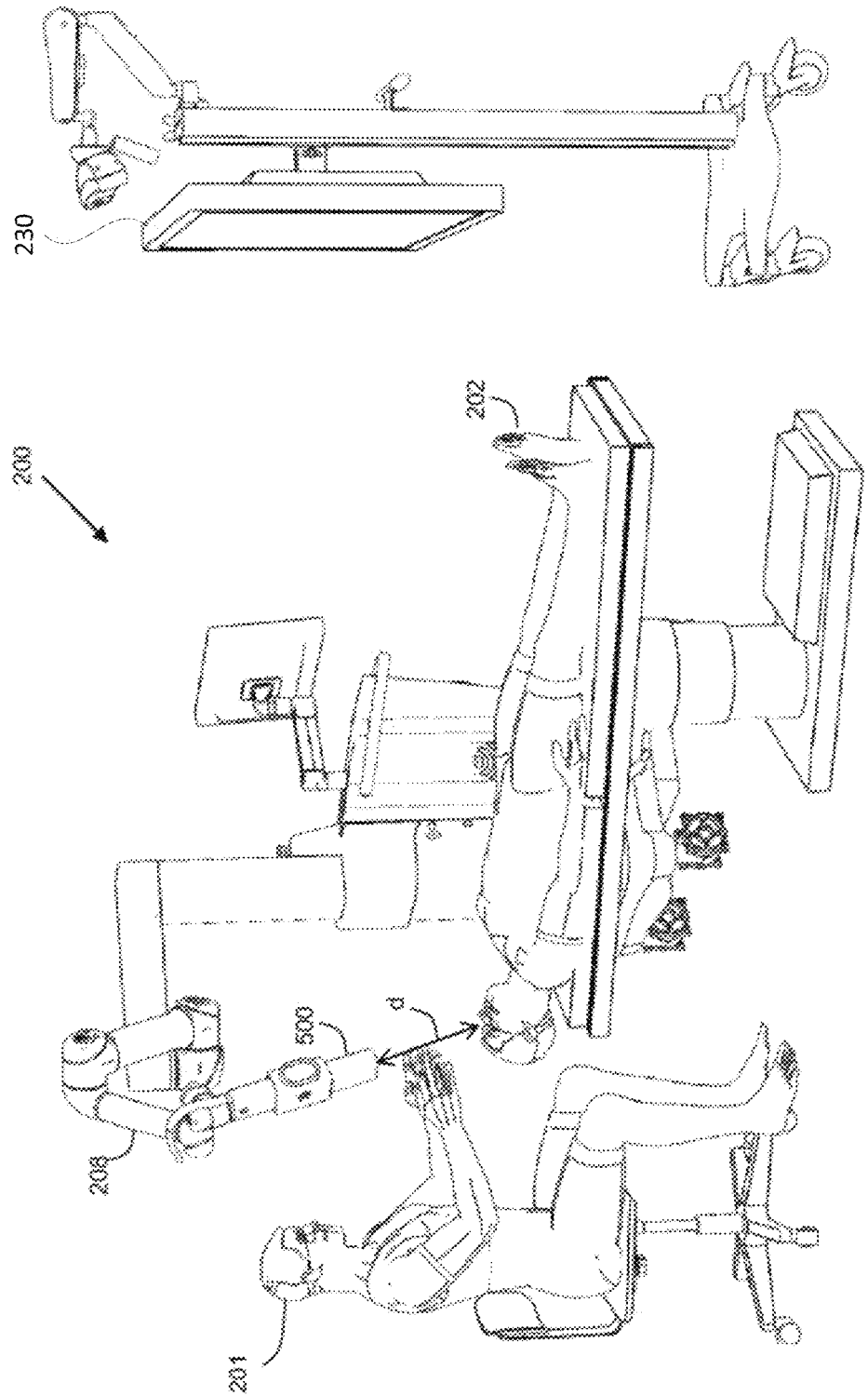
FIG. 4A shows the use of an example optical imaging system during a medical procedure.

FIG. 4A illustrates use of an example optical imaging system 500, described further below, in a medical procedure. Although FIG. 4A shows the optical imaging system 500 being used in the context of a navigation system environment 200 (e.g. using a navigation system as described above), the optical imaging system 500 may also be used outside of a navigation system environment.

An operator, typically a surgeon 201, may use the imaging system 500 to observe the surgical site (e.g. to look down an access port). The optical imaging system 500 may be attached to a positioning system 208, such as a controllable and adjustable robotic arm. The position and orientation of the positioning system 208, imaging system 500, and/or access port may be tracked using a tracking system, such as described for the navigation system 205. The distance between the optical imaging system 500 (more specifically, the aperture of the optical imaging system 500) and the viewing target may be referred to as the working distance.

The optical imaging system 500 may be designed to be used in a predefined range of working distance (e.g. in the range of between 15 and 75 centimeters). It should be noted that, if the optical imaging system 500 is mounted on the positioning system 208, the actual available range of working distance may be dependent on both the working distance of the optical imaging system 500 as well as the workspace and kinematics of the positioning system 208. In some embodiments, the optical imaging system 500 may include a manual release button that, when actuated, enables the optical imaging system to be positioned manually. For example, the controller of the optical imaging system 500 may be responsive to manual control input received via a user interface.

Figure 4B:
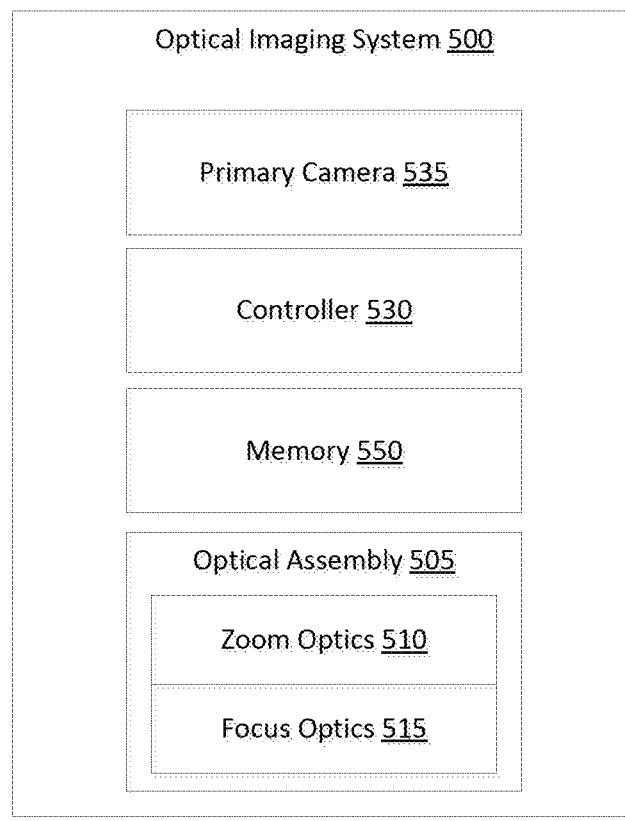
FIG. 4B is a block diagram illustrating components of an example optical imaging system 500.

Reference is now made to FIG. 4B, which shows components of an example optical imaging system 500. The optical imaging system 500 includes a primary camera (or video-scope) 535. The primary camera 535 may be a high-definition (HD) camera that captures image data from the optical assembly. The optical imaging system 500 may also include an optical assembly 505. The optical assembly 505 may include optics (e.g. lenses, optical fibers, etc.) for focusing and zooming on the viewing target. The optical assembly 505 may include zoom optics 510 and focus optics 515. Each of the zoom optics 510 and focus optics 515 are independently moveable within the optical assembly, in order to adjust the zoom and focus, respectively. The optical assembly 505 may include an aperture which may be adjustable.

The optical imaging system 500 also includes a memory 550 and a controller 530 coupled to the memory 550. The controller 530 may comprise one or more processors (e.g. micro-processors), programmable logic devices (e.g. field-programmable gate arrays, or FPGAs), application-specific integrated circuits (ASICs), or combinations thereof. In at least some embodiments, the controller 530 is configured to control operation of a zoom actuator and a focus actuator. The controller 530 may receive control input indicating a desired zoom and/or focus and, in response to receiving the input, the controller 530 may cause the zoom actuator and/or the focus actuator to move the zoom optics 510 and focus optics 515, respectively.

The controller 530 is also configured to control operation of the primary camera 535. The primary camera 535 may output camera data to the controller 530, which in turn transmits the data to an external system for viewing. The captured images can then be viewed on larger displays and may be displayed together with other relevant information, such as a wide-field view of the surgical site, navigation markers, etc.

In at least some embodiments, the primary camera 535, optical assembly 505 (including the zoom optics 510 and focus optics 515), controller 530, and memory 550 may all be housed within a single housing of the optical imaging system 500. The housing may be provided with a frame on which trackable markers may be mounted to enable tracking by a navigation system. The optical imaging system 500 may be mountable on a moveable support structure, such as a positioning system (e.g. robotic arm) of a navigation system, a manually operated support arm, a ceiling-mounted support, a moveable frame, or other support structure. In some embodiments, the optical imaging system 500 may include a support connector, such as a mechanical coupling, to enable the optical imaging system 500 to be mounted to and dismounted from the support structure.

FIGS. 5A-5E show different views of an example augmented optical imaging system 600. The augmented optical imaging system 600 includes one or more of the components of the optical imaging system 500. In particular, the augmented optical imaging system 600 includes a primary camera 602 for capturing an image of a target, zoom and focus optics, one or more light sources 610, and a controller (not shown) for controlling operation of the primary camera 602 and zoom, focus, and/or auxiliary optics.

In addition to these components, the augmented optical imaging system 600 includes a 3-D optics module 630. The 3-D optics module 630 extends the functionalities of the optical imaging system 500. In particular, the 3-D optics module 630 comprises an add-on component to the optical imaging system 500. In some embodiments, the 3-D optics module 630 may be separable from the optical imaging system 500. For example, the 3-D optics module 630 may be a separate device/module that can be mounted to the optical imaging system 500 or components thereof, such as the primary camera 602. In such embodiments, the optical imaging system 500 may refer to that part of the augmented optical imaging system 600 which is separate from the 3-D optics module 630. The 3-D optics module 630 may enable the augmented optical imaging system 600 to obtain 3-D information of a viewing target.

Figure 6B:
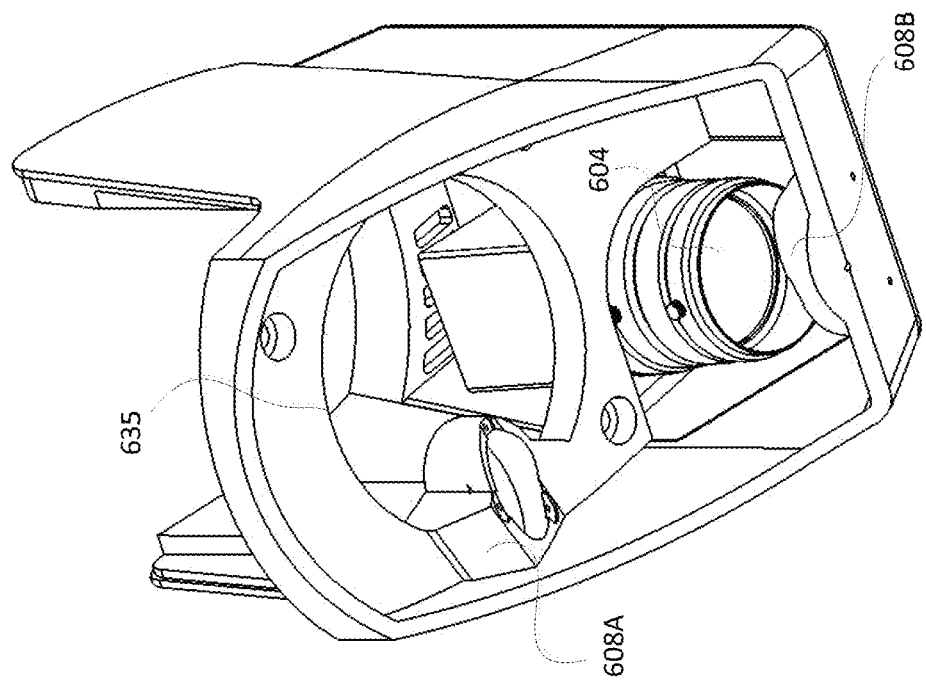
FIGS. 6A-6B show different perspective views of an example module for augmenting an optical imaging system.
Figure 6A:
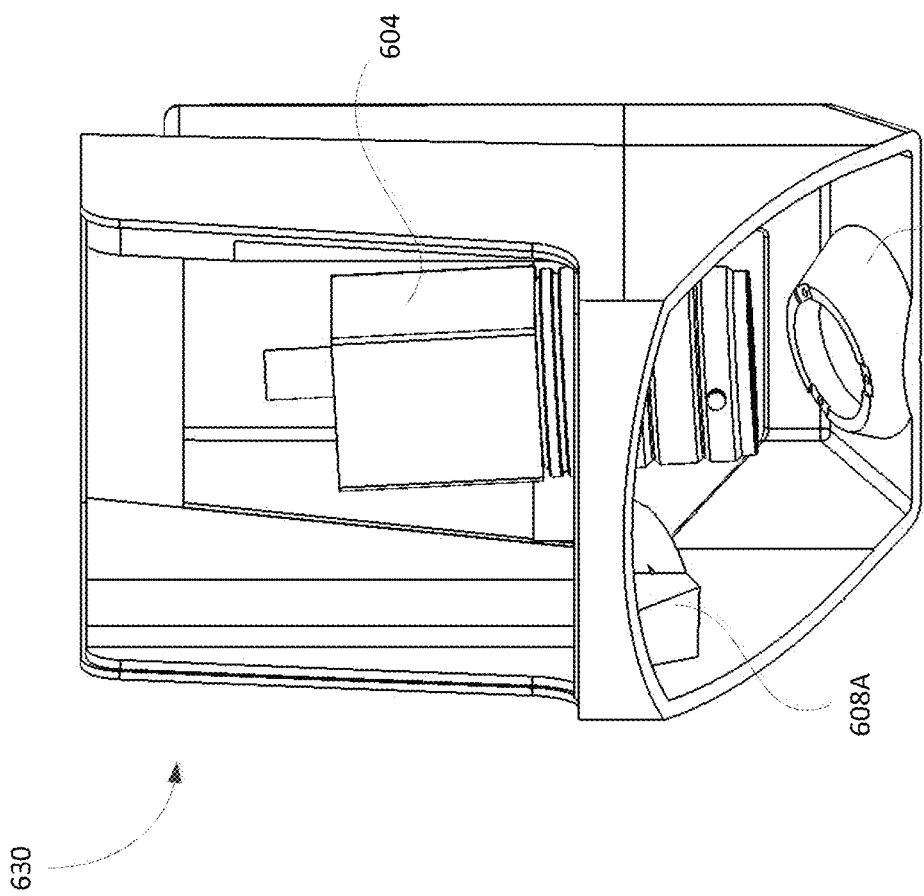
Figure 7A:
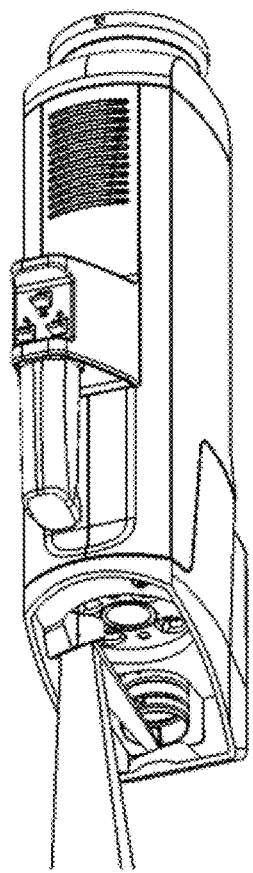
FIGS. 7A-7D show optical paths for the cameras of the augmented optical imaging system of FIGS. 5A-5E.
Figure 7B:
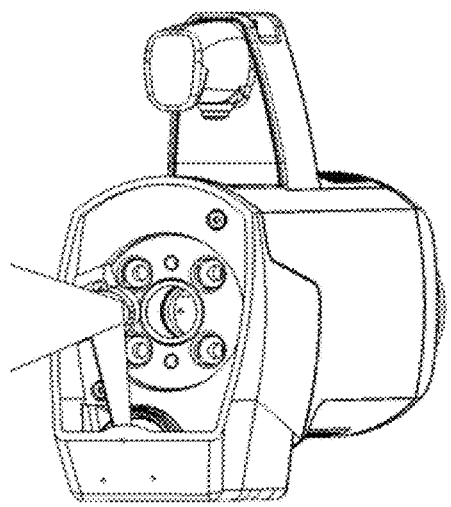
Figure 7C:
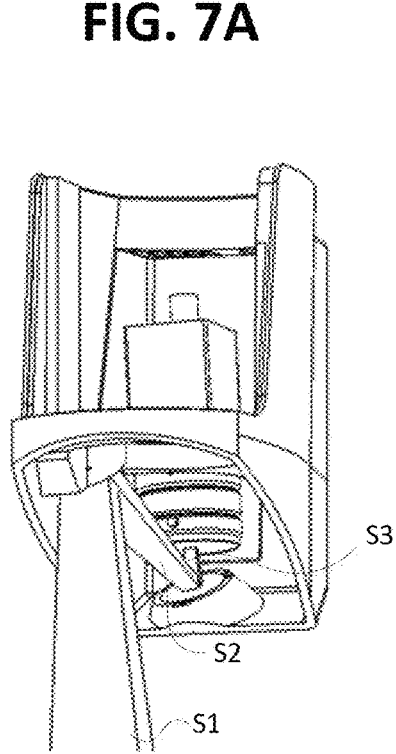
Figure 7D:
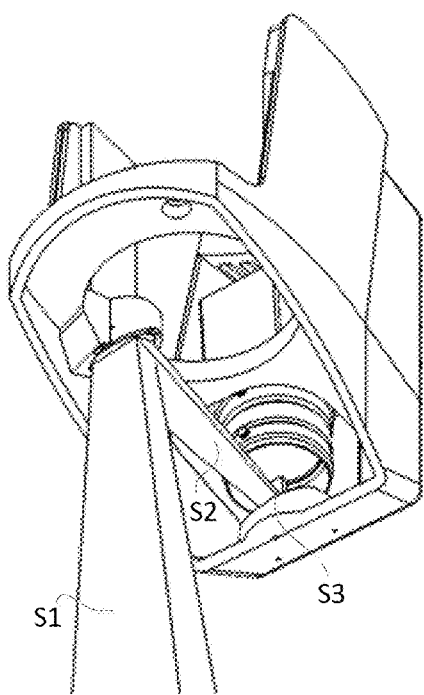

As shown in FIGS. 6A-6B and FIGS. 7C-7D, the 3-D optics module 630 includes a secondary (e.g. outrigger) camera 604 for capturing an image of a target and a pair of path folding mirrors 608A and 608B. The secondary camera 604 has a wide-field view, and may have at least one of fixed zoom optics, fixed focus optics, or digital zoom capability. The path folding mirrors 608A and 608B are positioned in spaced relation to each other. Specifically, the path folding mirrors 608A and 608B are angled with respect to each other such that they are disposed in an optical path between a target being imaged by the secondary camera 604 and a lens of the secondary camera 604. That is, light reflected off a surface of the imaged target traverses a path that includes the path folding mirrors 608A and 608B. The optical path of the secondary camera 604 thus includes, at least, a first segment (S1) between the target and a reflective surface of a first path folding mirror 608A, a second segment (S2) between the reflective surface of the first path folding mirror 608A and a reflective surface of a second path folding mirror 608B, and a third segment (S3) between the reflective surface of the second path folding mirror 608B and a lens of the secondary camera 604. Accordingly, in at least some embodiments, the path folding mirrors 608A and 608B are selectively positioned based on a position of the lens of the secondary camera 604. This optical path is shown in FIGS. 7C-7D.

The 3-D optics module 630 is configured to be connected to an optical imaging system in order to augment the functionalities of the optical imaging system. In particular, the 3-D optics module 630 may be affixed directly to an optical imaging system and secured thereto by a suitable fastening mechanism. As shown in FIG. 6B, the 3-D optics module 630 defines a chamber/bore which is sized to receive the primary camera 602 when the 3-D optics module 630 is secured to the optical imaging system. The optics of the primary camera 602 align with the opening 635 defined on the 3-D optics module 630. In some embodiments, the primary camera 602 may extend through the opening 635 when the 3-D optics module 630 is secured to the optical imaging system.

Returning to FIGS. 5A-5E, a controller of the augmented optical imaging system 600 is configured to receive a first image from the primary camera 602 and a second image from the secondary camera 604. For example, the primary camera 602 and secondary camera 604 may acquire real-time camera data (e.g. videos, images, etc.) depicting a target. In at least some embodiments, the primary camera 602 and the secondary camera 604 are positioned such that the optical axis of the primary camera 602 is co-planar with the optical axis of the secondary camera 604. The primary camera 602 may be offset both vertically and horizontally relative to the secondary camera 604. In some embodiments, the primary camera 602 and the secondary camera 604 may be offset only horizontally.

Figure 8:
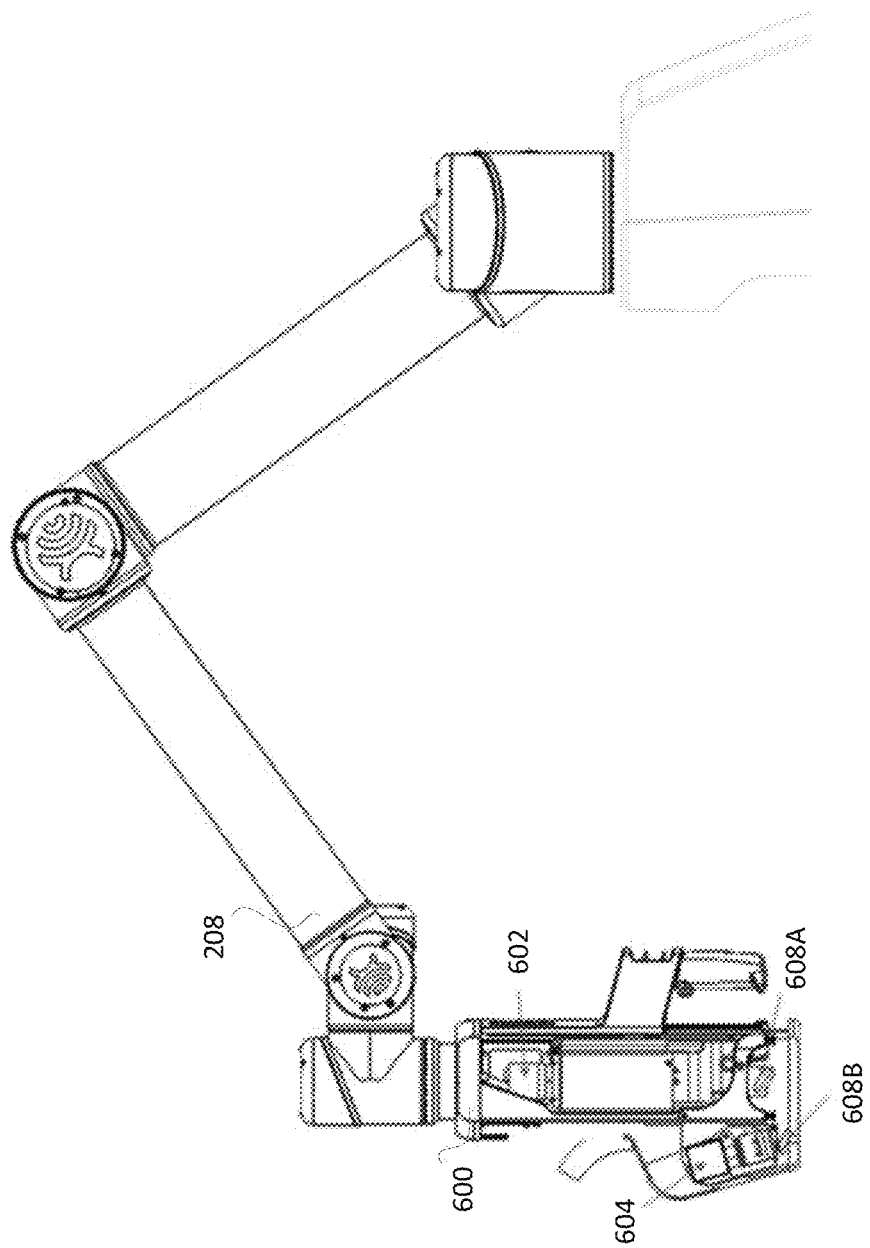
FIG. 8 is a partial side cross-sectional view of the augmented optical imaging system mounted on a positioning system.

FIG. 8 shows the augmented optical imaging system 600 mounted to a positioning system 208 (e.g. a robotic arm) of a navigation system. The augmented optical imaging system 600 is shown with a housing that encloses the zoom and focus optics, the primary camera 602, the secondary camera 604, and a pair of path folding mirrors 608A and 608B.

Furthermore, FIG. 8 shows the secondary camera 604 being angled with respect to the primary camera 602. In particular, the primary camera 602 is positioned substantially vertically within the housing of the augmented optical imaging system while the secondary camera 604 is positioned at an angle with respect to the vertical. The path folding mirrors 608A and 608B are disposed in the 3-D optics module 630 such that the optical path for the secondary camera 604 does not intersect the optical path for the primary camera 602. Specifically, the path folding mirrors 608A and 608B are positioned so that the optical path for the secondary camera 604 does not obstruct the substantially vertical line of sight of the primary camera 602.

Figure 9:
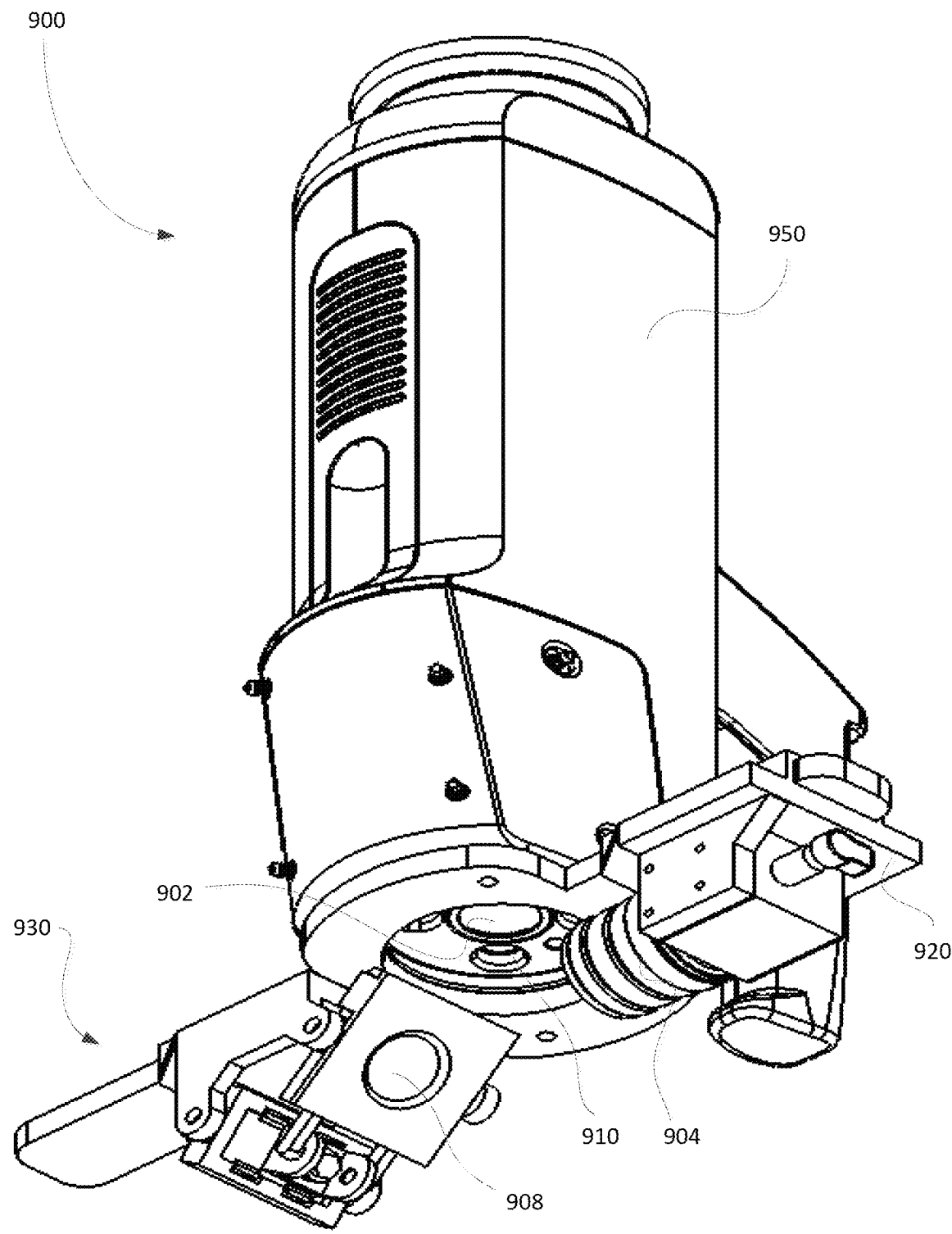
FIG. 9 shows a perspective view of another example augmented optical imaging system.

FIG. 9 is a perspective view of another example augmented optical imaging system 900. The augmented optical imaging system 900 may be incorporated into a digital microscope system, and more generally, a medical navigation system. The augmented optical imaging system 900 includes an optical imaging system 950 and a 3-D optics module 930. The optical imaging system 950 includes, at least, a primary camera 902 for imaging a target and one or more light sources 910. The 3-D optics module 930 may be integral to the optical imaging system 950, or it may be a separable add-on component which can be secured to the optical imaging system 950. The 3-D optics module 930 includes a secondary camera 904 and a single path folding mirror 908. As shown in FIG. 9, the position of the path folding mirror 908 may be variable. For example, in some embodiments, a relative angle of the reflective surface of the path folding mirror 908 with respect to a lens of the secondary camera 904 is adjustable, either manually or via a control input. An actuator associated with the path folding mirror 908 may be controlled by a controller (not shown) of the augmented optical imaging system 900. In other embodiments (not shown), the actuator may be manually moved to configure the relative angle.

In the example of FIG. 9, the secondary camera 904 is positioned substantially orthogonal to the primary camera 902. In particular, the primary camera 902 is directed vertically downward, while the secondary camera 904 is directed substantially horizontally. The 3-D optics module 930 may include a plate 920 which can be secured to the optical imaging system 950. The plate 920 is generally planar and elongate, and is disposed generally orthogonal to the optical imaging system 950. That is, the plate 920 is substantially horizontal when secured to the optical imaging system 950. As shown in FIG. 9, the secondary camera 904 may be affixed to the plate 920.

The path folding mirror 908 is disposed in an optical path between a target being imaged and a lens of the secondary camera 904. That is, an optical path of the secondary camera 904 traverses a path defined by a first segment between the target and a reflective surface of the path folding mirror 908 and a second segment between the reflective surface of the path folding mirror 908 and a lens of the secondary camera 904. The path folding mirror 908 is located on the 3-D optics module 930 such that it does not obstruct a (vertical) line of sight of the primary camera 902. That is, the path folding mirror 908 does not interfere with an optical path of the primary camera 902.

Figure 10:
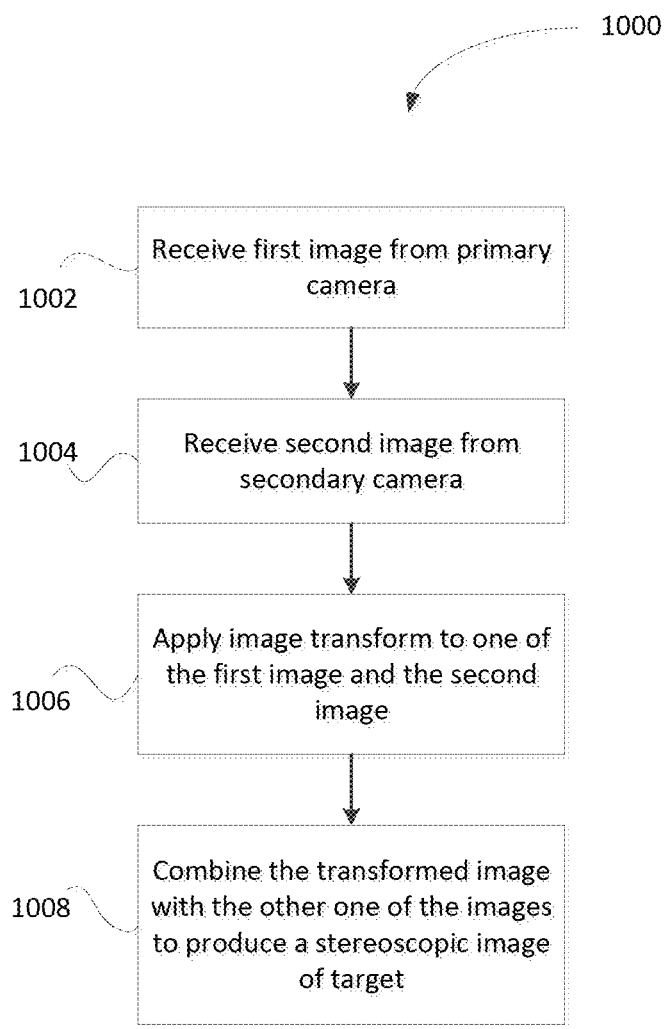
FIG. 10 shows, in flowchart form, an example method of generating a stereoscopic image of a target using the augmented optical imaging system of FIGS. 5A-5E.

Reference is now made to FIG. 10 which shows, in flowchart form, an example method 1000 for generating a 3-D image of a target using an augmented optical imaging system. The method 1000 may be implemented in a digital microscope system. For example, the method 1000 may be implemented by a controller of an augmented optical imaging system integrated into a digital microscope, or similar processing unit for controlling operations of cameras of an augmented optical imaging system.

In operation 1002, the controller receives a first image from the primary camera, and in operation 1004, the controller receives a second image from the secondary camera. The controller then applies an image transform to one of the first image and the second image, in operation 1006. In at least some embodiments, the image transform is a homographic transform. In particular, the image transform may implement a homography used for image rectification. With known relative camera positions, the homography warps one of the images such that the first and second images appear as if they have been taken with only a horizontal displacement, thereby simplifying the stereo matching process in generating 3-D visualization of the target. In some embodiments, the controller may be configured to determine a working distance (i.e. stand-off distance) between the target and an aperture of the optical imaging system (or opening for the cameras' lines of sight) and determine the image transform to be applied to the one of the images based on the working distance.

The determination of the homographic transform to apply in operation 1006 may be done based on an interpolation scheme. That is, the controller may be configured to interpolate between two or more calibration homographies. Further, the controller may search a range of interpolated homographies and determine a "best" homography transform to apply to images from the secondary camera in generating 3-D visualizations. This may be done by, for example, applying each of a plurality of homographic transforms (i.e. warping) to images from the secondary camera and computing a metric that represents image correspondence between the warped images and the corresponding images from the primary camera. The controller may take, as inputs, a transform of an image from the secondary camera and a corresponding (i.e. captured substantially concurrently) image from the primary camera, and output a value for a relevant metric. A homography that produces an optical value for the metric in question can be selected as the "best" homography.

Various different metrics may be suitably employed by the controller in the image comparisons. The metric may, for example, comprise correlation, mutual information, difference of squares, etc. The computation of the metric may be done for the entire range of interpolated homography transforms under investigation. Depending on the metric that is used, the controller may look for either a local maximum value or a local minimum value in identifying the transform that results in highest image correspondence, or best match. For example, if a difference of squares metric is used, the controller would look for the homography producing the lowest value for the metric from among the interpolated transforms. As another example, if image correlation is the metric used, a homography that produces the highest value for the metric may be selected as the best homography.

In operation 1008, the controller combines the transformed image and the other one of the images to generate a stereoscopic image of the target. In at least some embodiments, the controller may perform calibration of the zoom of the primary and secondary cameras prior to generating the stereoscopic image. For example, if the augmented optical imaging system has been moved to a significant degree or a predefined period of time has elapsed since last calibration of the cameras, the controller may be configured to automatically calibrate zoom. In some embodiments, the augmented optical imaging system may auto-calibrate for a plurality of predefined stand-off distances.

Figure 5C:
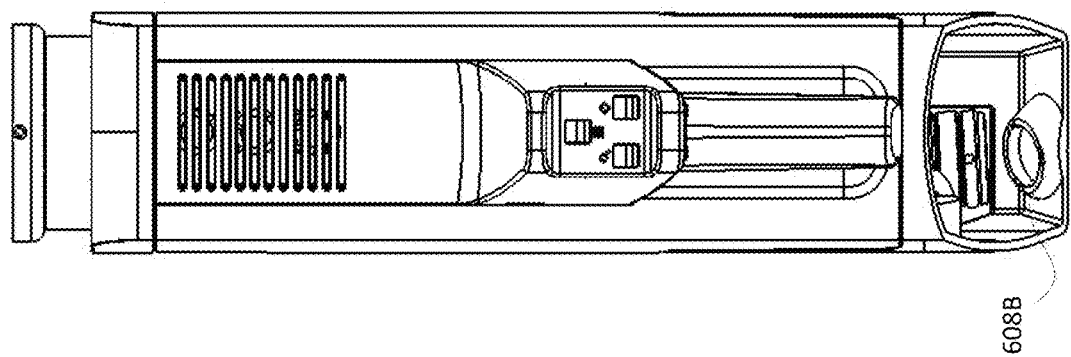
FIGS. 5A-5E show different views of an example augmented optical imaging system.
Figure 5B:
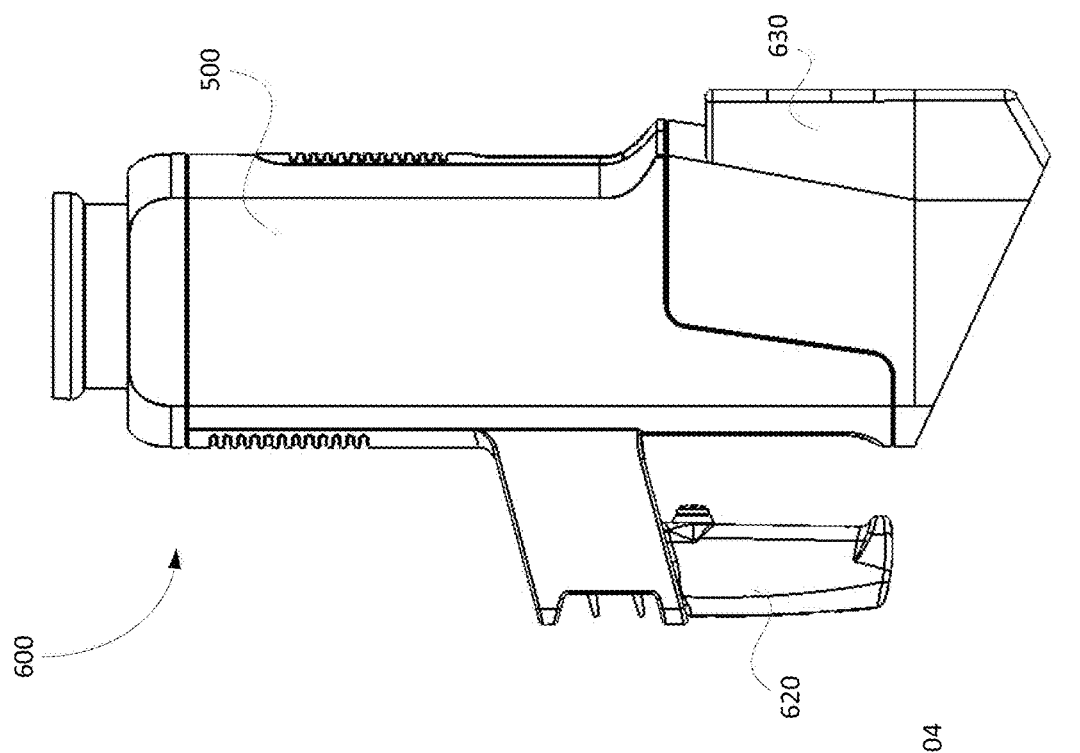
Figure 5A:
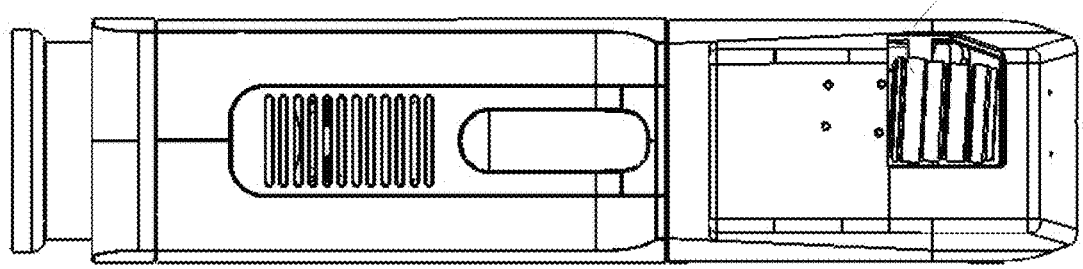
Figure 5D:
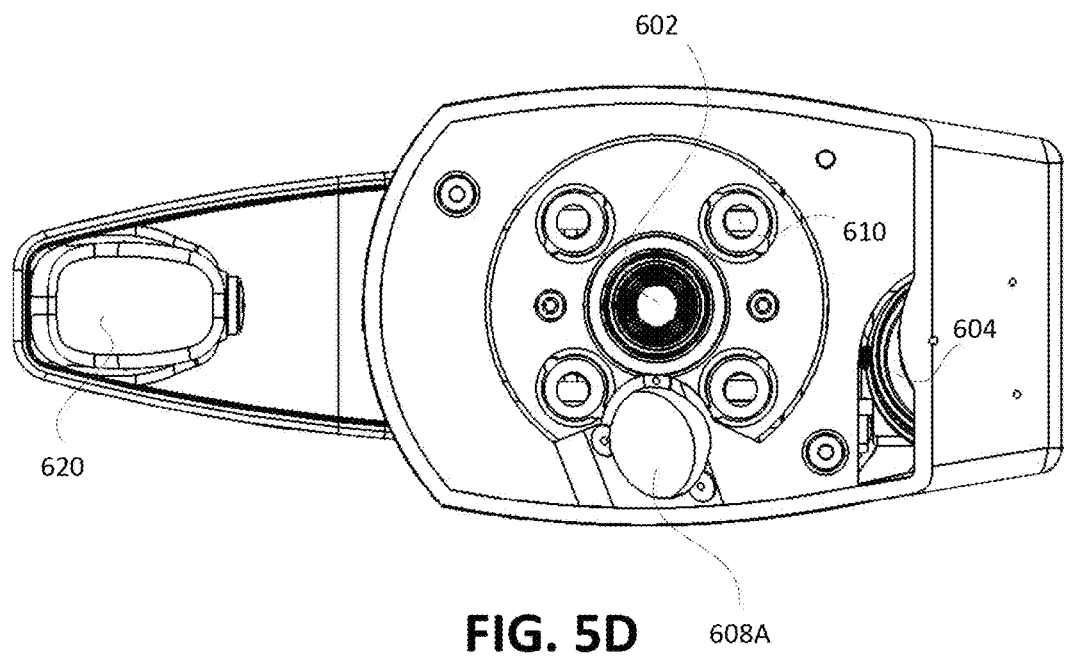
Figure 5E:
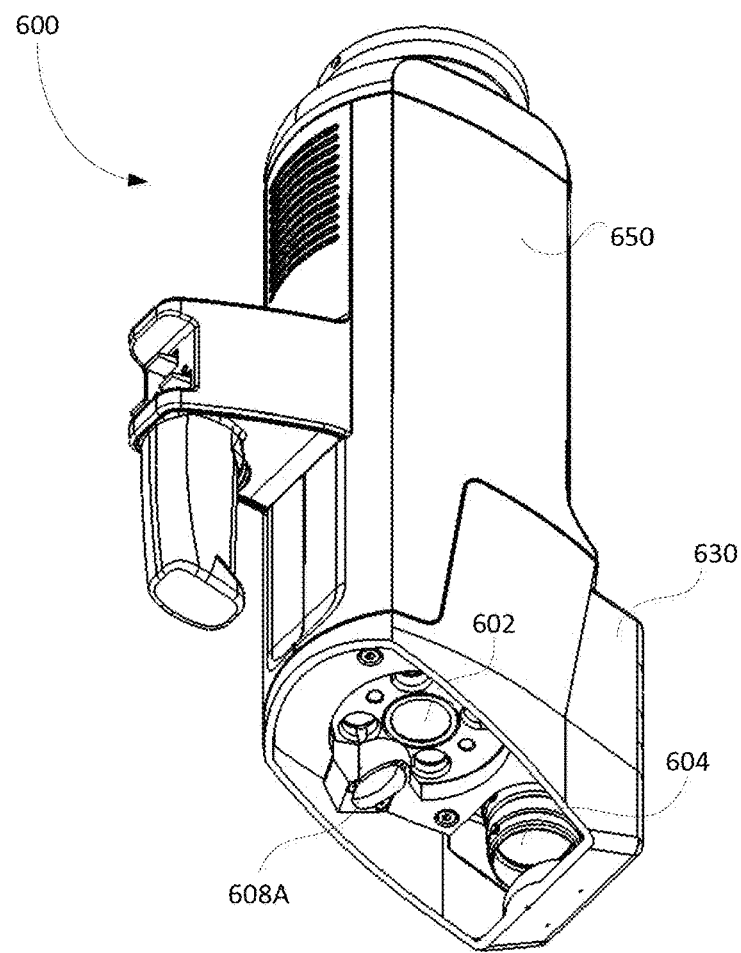

Returning to FIG. 4A, the navigation system 200 may be adapted to provide 3-D information of a viewing target. Specifically, the navigation system 200 may incorporate a 3-D visualization setup for use during a medical procedure. As shown in FIG. 5A, the 3-D visualization setup may include an optical imaging system 500 that includes a primary camera, a secondary camera, and at least one path folding mirror. In at least some embodiments, the primary camera (which may be the optical head of the optical imaging system 500), the secondary camera, and the at least one path folding mirror may be housed within a single housing. The optical imaging system 500 may be connected to a positioning system 208, such as a mechanical arm or stand, which is controllable, adjustable, and moveable. The optical imaging system 500 may be mounted to the positioning system 208 such that the positioning system 208 can position and orient the optical imaging system 500.

Operation of the optical imaging system 500 may be controlled by a processing unit of the optical imaging system 500 or the navigation system 200. The processing unit is configured to generate 3-D stereoscopic images of a viewing target, based on images acquired by the primary and secondary cameras. For example, the processing unit may implement a method for generating 3-D information, such as method 1000 of FIG. 10. The processing unit may also be configured to implement a calibration module for calibrating images from the cameras. The calibration module may, for example, determine a current position and orientation of the cameras of the optical imaging system 500. The calibration module may also determine transforms (e.g. homographies) to apply to images of the cameras for providing 3-D visualization of the viewing target.

The optical imaging system 500 may transmit data to the controller or to an external system, such as an external work station. The image data acquired by the optical imaging system 500 is used to generate 3-D stereoscopic images of the viewing target. The stereoscopic image information may be displayed, for example, on a 3-D display device 230 (e.g. 3-D monitor) that is viewable using 3-D glasses donned by the surgeon 201 during a procedure. The 3-D information may also be useful for an augmented reality (AR) display. For example, an AR display system may use information acquired by the navigation system 200 and overlay 3-D images of a target specimen on a real-time image captured by the cameras.

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. An optical imaging system for imaging a target during a medical procedure, the system comprising:
   a first camera for capturing a first image of the target;
   a second wide-field camera;
   at least one path folding mirror disposed in an optical path between the target and a lens of the second camera, the second camera configured to capture a second image of the target that is reflected by the at least one path folding mirror to the lens of the second camera; and
   a processing unit for receiving the first image and the second image, the processing unit being configured to:
      apply an image transform to one of the first image and the second image; and
      combine the transformed image with the other one of the images to produce a stereoscopic image of the target.

2. The optical imaging system of claim 1, wherein the first camera, the second camera, and the at least one path folding mirror are housed within a single housing.

3. The optical imaging system of claim 1, wherein the second camera and the at least one path folding mirror are included in an add-on module for mounting to the first camera.

4. The optical imaging system of claim 1, wherein the at least one path folding mirror comprises a first mirror and a second mirror that are selectively positioned based on a position of the lens of the second camera, the first mirror and the second mirror being angled with respect to each other.

5. The optical imaging system of claim 4, wherein the first mirror is selectively positioned and angled with respect to the target so as to reflect an image of the target to the second mirror, and the second mirror is selectively positioned and angled so as to reflect the image of the target from the first mirror to the lens of the second camera.

6. The optical imaging system of claim 1, wherein the first camera and the second camera are positioned such that an optical axis of the first camera is co-planar with the optical axis of the second camera.

7. The optical imaging system of claim 1, wherein the image transform is a homographic transform.

8. The optical imaging system of claim 1, wherein the processing unit is further configured to:
   determine a working distance between the target and an aperture of the optical imaging system; and
   determine the image transform based on the working distance.

9. The optical imaging system of claim 1, wherein the optical imaging system is configured to be mountable onto a moveable support structure.

10. The optical imaging system of claim 9, wherein the optical imaging system further comprises a support connector to enable the optical imaging system to be removably mounted onto the moveable support structure.

11. The optical imaging system of claim 10, wherein the moveable support structure comprises one of a robotic arm, a manually-operated support arm, or a moveable support frame.

12. The optical imaging system of claim 11, further comprising a manual release button that, when actuated, enables the optical imaging system to be positioned manually.

13. The optical imaging system of claim 12, wherein the processing unit is responsive to control input received via a user interface.

14. The optical imaging system of claim 1, further comprising one or more light sources.

15. The optical imaging system of claim 1, wherein the second camera has at least one of fixed zoom optics or fixed focus optics.

16. The optical imaging system of claim 1, wherein the second camera is fixedly coupled to the first camera.

17. A method of generating a stereoscopic image of a target in a medical procedure using an optical imaging system, the method comprising:
 receiving, from a first camera of the optical imaging system, a first image of the target;
 receiving, from a second camera of the optical imaging system, a second image of the target that is reflected by at least one path folding mirror to a lens of the second camera, the at least one path folding mirror being disposed in an optical path between the target and the lens of the second camera;
 applying an image transform to one of the first image and the second image; and
 combining the transformed image with the other one of the images to produce the stereoscopic image of the target.

18. The method of claim 17, wherein the image transform is a first homographic transform.

19. The method of claim 17, further comprising:
 determining a working distance between the target and an aperture of the optical imaging system; and
 determining the image transform based on the working distance.

20. The method of claim 18, further comprising selecting the first homographic transform from a plurality of homographic transforms, wherein the selecting comprises:
 for each of the plurality of homographic transforms:
  applying the homographic transform to the second image;
  computing an image correspondence metric between the transformed second image and the first camera, and
 selecting the homographic transform that is associated with an optimal value of the image correspondence metric from the plurality of homographic transforms as the first homographic transform.

* * * * *